(12) United States Patent
Umemura

(10) Patent No.: US 6,624,411 B2
(45) Date of Patent: Sep. 23, 2003

(54) METHOD OF PRODUCING A BROAD-BAND SIGNAL FOR AN ION TRAP MASS SPECTROMETER

(75) Inventor: Yoshikatsu Umemura, Kyoto-fu (JP)

(73) Assignee: Shimadzu Corporation, Kyoto (JP)

( * ) Notice: Subject to any disclaimer, the term of this patent is extended or adjusted under 35 U.S.C. 154(b) by 407 days.

(21) Appl. No.: 09/769,483

(22) Filed: Jan. 26, 2001

(65) Prior Publication Data

US 2001/0010355 A1 Aug. 2, 2001

(30) Foreign Application Priority Data

Jan. 31, 2000  (JP) ........................................ 2000-022370

(51) Int. Cl.[7] ............................. B01D 59/44; H01J 49/00
(52) U.S. Cl. ........................................ 250/292; 250/282
(58) Field of Search ................................. 250/281, 282, 250/292

(56) References Cited

U.S. PATENT DOCUMENTS

| | | | | |
|---|---|---|---|---|
| 3,937,955 A | * | 2/1976 | Comisarow et al. ........ 250/282 |
| 4,761,545 A | * | 8/1988 | Marshall et al. ............ 250/291 |
| 5,198,665 A | * | 3/1993 | Wells .......................... 250/282 |
| 5,200,613 A | * | 4/1993 | Kelley ......................... 250/282 |
| 5,302,826 A | * | 4/1994 | Wells .......................... 250/292 |
| 5,396,064 A | * | 3/1995 | Wells .......................... 250/282 |
| 5,457,315 A | * | 10/1995 | Wells et al. ................. 250/282 |

\* cited by examiner

*Primary Examiner*—Bruce Anderson
(74) *Attorney, Agent, or Firm*—Armstrong, Westerman & Hattori, LLP

(57) ABSTRACT

A method of producing a broad-band signal including a plurality of component frequencies of regular or irregular intervals, where the broad-band signal is used to apply an alternating voltage to the end cap electrodes of an ion trap mass spectrometer. The method includes the following steps: (S3) a sinusoidal signal having one of the component frequencies with 0° initial phase angle is generated; (S4) the sinusoidal signal is added to a current temporary superposed signal to produce an addition signal; (S5) the sinusoidal signal is subtracted from the current temporary superposed signal to produce a subtraction signal; (S6–S12) either of the addition signal or the subtraction signal is selected that has a smaller amplitude as a next temporary superposed signal; and (S13) the steps are repeated for all the component frequencies.

3 Claims, 4 Drawing Sheets

SINGLE FREQUENCY

BROAD BAND FREQUENCY DISTRIBUTION

NOTCHED FREQUENCY DISTRIBUTION

METHOD OF PRODUCING A BROAD-BAND SIGNAL FOR AN ION TRAP MASS SPECTROMETER

The present invention relates to a method of producing a broad-band signal applied to the end cap electrodes of an ion trap mass spectrometer for measuring in various analyzing modes.

BACKGROUND OF THE INVENTION

An ion trap mass spectrometer is composed of a ring electrode having a hyperboloid-of-one-sheet-of-revolution internal surface and a pair of end cap electrodes having hyperboloid-of-two-sheets-of-revolution internal surfaces facing each other with the ring electrode therebetween. When a radio frequency AC (Alternating Current) voltage is applied between the ring electrode and the end cap electrodes, a quadrupole electric field is generated in the space surrounded by these electrodes (the space is hereinafter referred to as the "ion trap space"), in which ions produced within the ion trap space or ions introduced there from outside can be trapped.

In an ion trap mass spectrometer, various analyzing modes are possible by applying corresponding appropriate voltages to the end cap electrodes after ions are trapped in the ion trap space. When an AC voltage of a specific frequency $f_a$, as shown in FIG. 6A, is applied to the end cap electrodes, only ions having a specific mass number (mass/charge) corresponding to the frequency $f_a$ resonate and oscillate, and are discharged from the ion trap space. If collision gas is introduced in the ion trap space and the voltage is properly applied, ions having a specific mass number are excited and fragmented. This method is used in an MS/MS analysis.

When an AC voltage signal containing frequency components ranging from $f_b$ to $f_c$, as shown in FIG. 6B, is applied to the end cap electrodes, ions having several mass numbers corresponding to the frequency range $f_b$–$f_c$ are simultaneously resonated and discharged from the ion trap space. When an AC voltage signal devoid of frequency components ranging from $f_d$ to $f_e$ (which is called a notched frequency range), as shown in FIG. 6C, is applied to the end cap electrodes, ions having mass number corresponding to the frequency rage $f_d$–$f_e$ remain in the ion trap space and the other ions are discharged.

The voltage signal containing frequency components ranging from $f_b$ to $f_c$ as shown in FIG. 6B or that of notched frequency range as shown in FIG. 6C (which are hereinafter referred to as "broad-band signal") can be produced through a signal processing on a computer. In concrete, a broad-band signal can be produced by superposing (or adding) the component sinusoidal signals each having a singular frequency. If such component sinusoidal signals are simply superposed one by one, however, the amplitude of the resultant signal gradually increases and a large capacity power source is needed, which will increase the cost of such a device. Practically, therefore, when superposing the component sinusoidal signals, the initial phase angle of every sinusoidal signal is appropriately selected and shifted so that the amplitudes are cancelled with one another while the frequencies are preserved and properly incorporated in the resultant signal. The required dynamic range of the power source is thus suppressed.

One of conventional methods for finding such an appropriate initial phase angle of every component sinusoidal signal is as follows. When every sinusoidal signal is superposed to a temporary superposed signal, the initial phase angle of the sinusoidal signal is, starting from the 0°, shifted stepwisely by a certain amount (1°, for example), and the amplitude of the temporary superposed signal is examined to find out an appropriate initial phase angle that makes the amplitude minimum. This method is advantageous in assuredly finding the optimal initial phase angle for the minimum amplitude, but has a shortcoming in the enormous calculation that takes a long time even with a high-spec computer.

An improved method is described in the publication No. H07-509097 of Japanese translation of PCT international application as follows. The initial phase angle of every component sinusoidal signal is shifted by larger steps (10°, for example) to find out a rough optimal initial phase angle that brings about the nearest minimum amplitude, and the initial phase angle is shifted near the rough optimal initial phase angle by smaller steps (1°, for example) to find out an exactly optimal initial phase angle that makes the amplitude minimum. This method still requires a large amount of calculations, which is disadvantageous especially when the components of a frequency range are rearranged and a subsequent re-calculation is needed to find out new optimal initial phase angles of the component sinusoidal signals.

Further improvement to the method described above is known as follows. A hypothetical total signal containing all the frequency components possible and needed in designing a mass spectrometer is produced beforehand, where the optimal initial phase angles of all the component sinusoidal signals are found out and the component signals are added to produce the resultant total hypothetical signal. The hypothetical total signal and the data of the optimal initial phase angles of all the component sinusoidal signals are stored in a memory. When a signal containing a certain range of frequencies is required, component sinusoidal signals that are not contained in the range are excluded and subtracted from the total hypothetical signal based on the data of the optimal initial phase angles of the component signals.

It is true that the amplitude is minimum in the hypothetical total signal in the above-described method, but it is not necessarily true when some component signals are subtracted from the hypothetical total signal. There may be better initial phase angle or angles of the component sinusoidal signal or signals for producing a further reduced amplitude of a resultant signal.

Thus the conventional methods are not yet satisfactory in suppressing the dynamic range of a signal containing a range of frequency components. The present invention addresses the problem.

SUMMARY OF THE INVENTION

As explained above, there are two ways to approach the object of reducing the amplitude of a superposed signal: one is to add up component sinusoidal signals, and the other is to subtract unnecessary components from the total signal containing all the component sinusoidal signals. The former better assures the minimum amplitude of a resultant signal, but it requires a process of finding out optimal initial phase angles, where it takes a long time to generate a set of data of a sinusoidal signal and further enormous time to generate candidate sinusoidal signals having a variety of initial phase angles before the optimal initial phase angle is determined. The present inventor has studied the relation between the magnitude of the shifting step in finding out the optimal initial phase angle and the effect of suppressing the amplitude. The inventor has come to the following conclusion: the conventional knowledge that the smaller magnitude of the shifting step brings about the smaller amplitude of the superposed signal is not necessarily true. Instead, using either one of 0° shift and 180° shift of the initial phase angle for every component sinusoidal signal is sufficient, and there is no significant difference in the amplitude suppressing effect between the small step shifting approach and the two phase angle approach.

The inventor further devised a new method relating to the two phase angle approach. In place of adding the 180° shifted component sinusoidal signal, the 0° shifted component sinusoidal signal is subtracted. This method has a great advantage in that only 0° shifted sinusoidal signal is needed for every frequency in superposing a component signal of the frequency and there is no need of generating many candidate sinusoidal signals of diverse initial phase angles.

Therefore, according to the present invention, the method of producing a broad-band signal including a plurality of component frequencies of regular or irregular intervals, where the broad-band signal is used to apply an alternating voltage to end cap electrodes of an ion trap mass spectrometer, includes the steps:

a) generating a sinusoidal signal having one of the component frequencies;

b) adding the sinusoidal signal to a current temporary superposed signal to produce an addition signal;

c) subtracting the sinusoidal signal from the current temporary superposed signal to produce a subtraction signal;

d) selecting either of the addition signal or the subtraction signal that has a smaller amplitude as a next temporary superposed signal; and e) repeating the steps a)–d) for all the component frequencies.

Since there is no need to generate data of many candidate sinusoidal waves of different initial phase angles and no need to try many addition (superposition) of such candidate waves before finding a sinusoidal wave having an optimal initial phase angle according to the present invention, the processing time for producing a side range signal is greatly reduced compared to conventional methods. The effect of suppressing the resultant superposed signal is almost the same as conventional methods searching with smaller initial phase angle steps, so that the dynamic range of the voltage generator of an ion trap mass spectrometer can be made smaller and the cost can be reduced. This allows the user of the ion trap mass spectrometer to try various measurement conditions for the voltage applied to the end cap electrodes without worrying about the time needed to obtain he result.

The above-described invention is more easily understood by the description of a preferred embodiment referring to the attached drawings.

DESCRIPTION OF A PREFERRED EMBODIMENT

Figure 1:
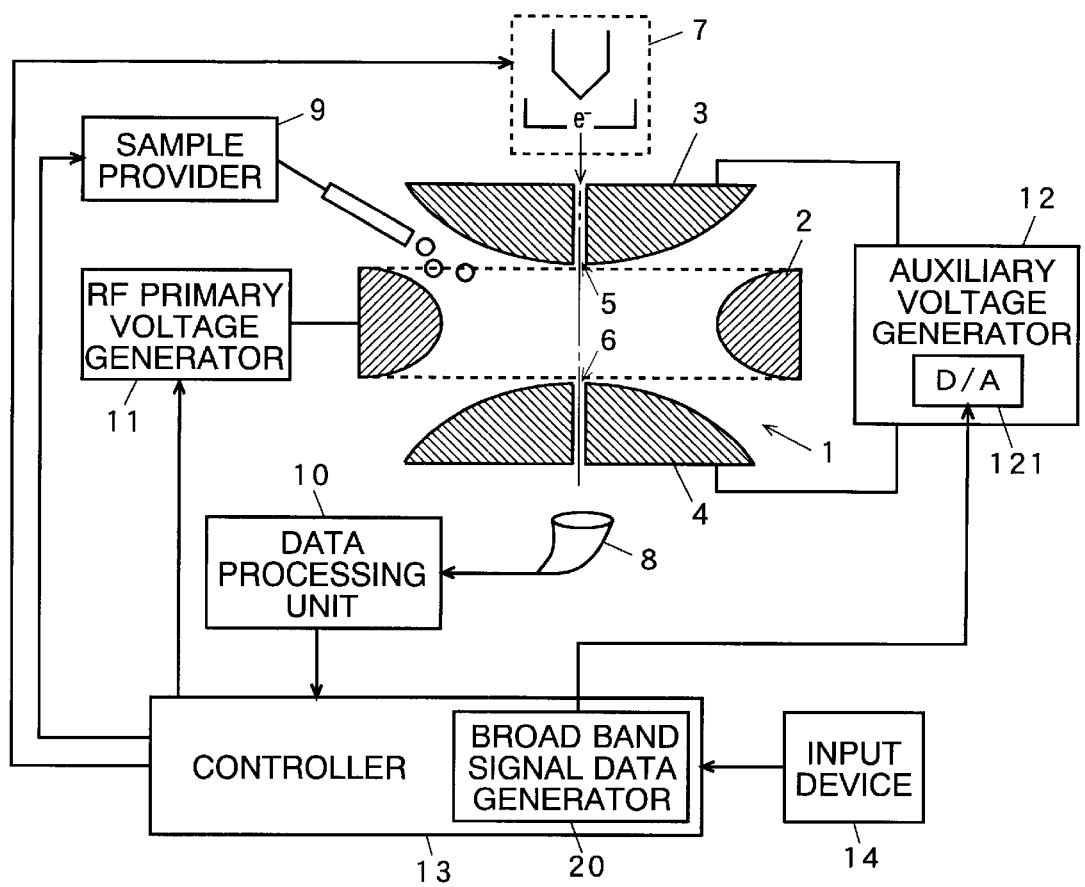
FIG. 1 is a block diagram of the main part of an ion trap mass spectrometer embodying the present invention.

FIG. 1 illustrates the main part of an ion trap mass spectrometer embodying the present invention.

An ion trap 1 is composed of a ring electrode 2 having a hyperboloid-of-one-sheet internal surface and a pair of end cap electrodes 3, 4 having hyperboloid-of-two-sheets internal surfaces facing each other with the ring electrode 2 therebetween. The ring electrode 2 is connected to an RF primary voltage generator 11, and the end cap electrodes 3, 4 are connected to an auxiliary voltage generator 12. A first through-hole 5 is formed at the center of the first end cap electrode 3, and a thermo-electron generator 7 is provided outside of the end cap electrode 3 and along the first through-hole 5. Electrons generated by the thermo-electron generator 7 are introduced in the ion trap space surrounded by the ring electrode 2 and the end cap electrodes 3, 4 through the first through-hole 5, and contact and ionize sample molecules introduced into the ion trap space from a sample provider 9. A second through-hole 6 is formed at the center of the second end cap electrode 4 and along the first through-hole 5, and a detector 8 is provided outside of the end cap electrode 4 and along the second through-hole 6. When the detector 8 detects an ion released from the ion trap space through the second through-hole 6, it sends a detection signal to a data processing unit 10.

The RF primary voltage generator 11 and the auxiliary voltage generator 12 are controlled by control signals sent from a controller 13 to generate AC voltages of given frequencies and amplitudes. The controller 13 is composed of a CPU, ROM, RAM (or plural of them) and other electronic devices, and sends out the control signals to such parts of the ion trap mass spectrometer based on measurement conditions given through the input device 14. The controller 13 includes a broad-band signal data generator 20 as one of its functional parts. The broad-band signal data generator 20 generates digital data of a broad-band signal based on the measurement conditions given through the input device 14 and sends the digital data to the auxiliary voltage generator 12. The auxiliary voltage generator 12 converts the digital data to an analog signal using a D/A converter 121, and the analog signal is applied to the end cap electrodes 3, 4.

Figure 2:
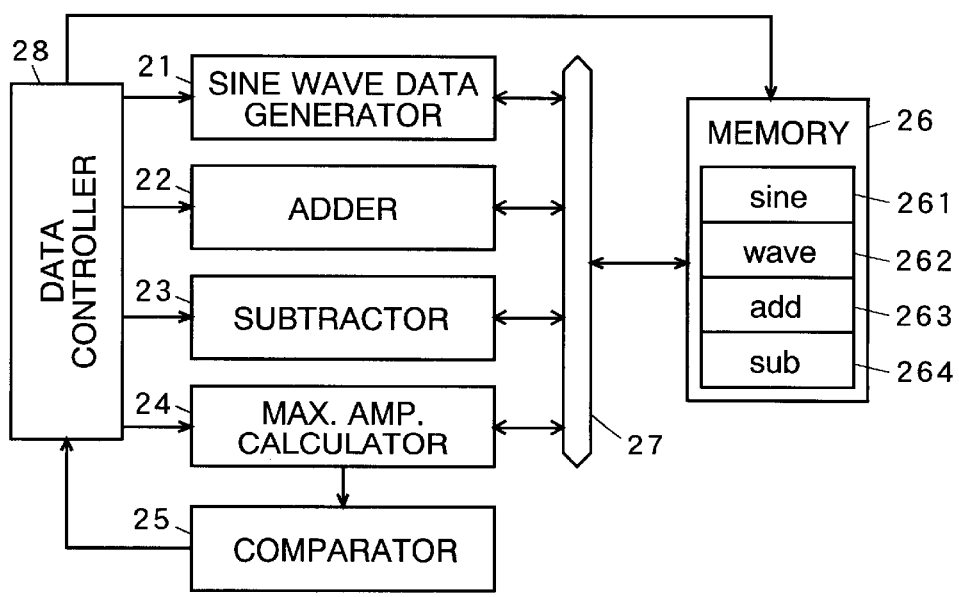
FIG. 2 is a block diagram showing the functional construction of the broad-band signal data generator.

FIG. 2 is a block diagram showing the functional construction of the broad-band signal data generator 20. The broad-band signal data generator 20 is composed of: a sinusoidal wave data generator 21 for generating a set of data of a sinusoidal wave having a designated frequency and a designated amplitude; an adder 22 for adding two sets of data each constituting a wave; a subtractor 23 for calculating a difference of two sets of data each constituting a wave; a maximum amplitude calculator 24 for calculating the maximum amplitude of a superposed wave of plural component sinusoidal waves; a comparator 25 for comparing the calculated maximum amplitudes; a memory 26 including a first memory (sine) 261 for storing data of sinusoidal waves, a second memory (wave) 262 for storing data of superposed waves, a third memory (add) 263 for storing data of added waves and a fourth memory (sub) 264 for storing data of subtracted waves; a data bus 27; and a data controller 28 for controlling the functional parts. Each of the first to fourth memories 261–264 contains n storage spaces, and each of the storage spaces has a bit capacity of no less than the bit size of one of many pieces of data constituting a wave.

Figure 3:
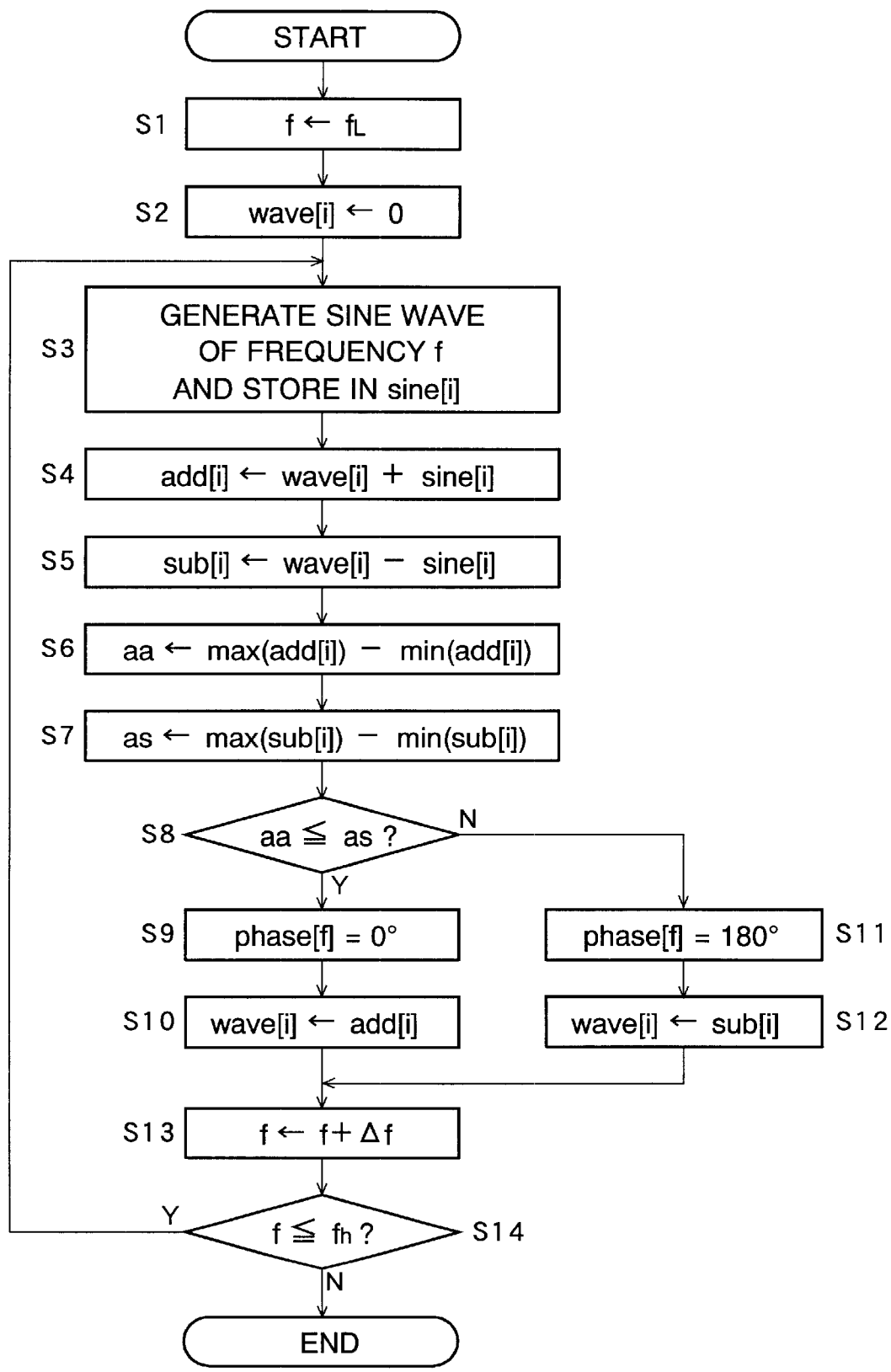
FIG. 3 is a flowchart of the process performed in the broad-band signal generator for generating a broad-band signal.

The process performed in the broad-band signal data generator 20 for generating data of a broad-band signal according to the present invention is described referring to the block diagram of FIG. 2 and the flowchart of FIG. 3. It is supposed here to produce a broad-band signal by superposing sinusoidal waves having frequencies of Δf (Hz) intervals ranging from $f_L$ (Hz) to $f_h$ (Hz). The amplitude of each sinusoidal wave can be arbitrary.

The number n of the storage spaces in each of the first to fourth memories 261–264 is determined as the smallest number of data necessary to build a finally produced broad-band signal wave. In concrete, the number n is determined as follows. When a number of sinusoidal waves are superposed or added, a beat arises from the combination of two sinusoidal waves having the smallest frequency difference. When, for example, a broad-band signal wave is produced by superposing a combination of some of sinusoidal waves differing by Δf=1 kHz from one another, a beat of 1 kHz or its integral multiples arises. Therefore, by repeating a unit wave of 1 msec-length which is one cycle fraction of a 1 kHz wave, a chronologically continuous broad-band signal wave is obtained. When an analog signal of a cycle is to be produced by a D/A converter, a piece of data is necessary for every conversion cycle of the D/A converter. When the conversion speed of the D/A converter is 10 MHz, for example, a wave of 1 msec-length is composed of 10000 pieces of data, in which case n=10000. This means that the number n is determined depending on the value of Δf and the conversion speed of the D/A converter.

In the flowchart of FIG. 3, [i] denotes that the processing is performed for every i of i=1 to n.

First, the frequency variable f is set at the lowest value $f_L$ (Step S1), and all of the n storage spaces of the second memory (wave) 262 are cleared (Step S2). Then the sinusoidal wave generator 21 generates a set of data constituting a sinusoidal wave of comparator 25 (Step S6). Similarly, the amplitude calculator 24 detects the maximum value and the minimum value of the wave data stored in the fourth memory (sub) 264, calculates the difference, and sends the data of the maximum difference ("subtraction amplitude") as to the comparator 25 (Step S7).

The comparator 25 determines whether the subtraction amplitude as is equal to or greater than the addition amplitude aa (Step S8). When as≧aa, the smaller maximum amplitude aa is preferred (Step S9) and the data in the third memory (add) 263, which represents the sinusoidal wave of 0° initial phase angle, are stored in the second memory (wave) 262 (Step S10). When, on the other hand, it is determined as<aa at Step S8, the smaller maximum amplitude as is preferred (Step S11) and the data in the fourth memory (sub) 264, which represents the sinusoidal wave of initial phase angle 180°, are stored in the second memory (wave) 262 (Step S12). This concludes a superposition of a sinusoidal wave of a frequency.

Then the frequency variable f is renewed by adding a frequency interval Δf to the current frequency variable f (Step S13), and it is determined whether the value of the renewed frequency variable f is equal to or less than the upper limit value $f_h$ (Step S14). When f≦$f_h$, the process returns to Step S3 to repeat the above processing for the sinusoidal wave of the renewed frequency f.

In the meantime, through the repetition of the above processings, sinusoidal waves of frequencies different from one frequency f and having a predetermined amplitude, and stores the data to the first memory (sine) 261 (Step S3). Then the data stored in the second memory (wave) 262, which are zero at first, and the data stored in the first memory (sine) are retrieved, added by the adder 22, and the resultant data (sum) are stored in the third memory (add) 263 (Step S4). Also the data retrieved from the first memory (sine) 261 is subtracted from the data retrieved from the second memory (wave) 262 by the subtractor 23, and the resultant data (difference) are stored in the fourth memory (sub) 264 (Step S5). The addition and the subtraction are done for every storage space.

Since a subtraction of a wave is equal to an addition of the reversed wave of the same wave, a subtraction of a sinusoidal wave is equal to an addition of the same sinusoidal wave with the phase shifted 180°. When the Steps S4 and S5 are performed for the first time, the content of the second memory (wave) 262 is zero due to the processing of Step S2. Therefore, the data of the sinusoidal wave generated in Step S3 are stored as they are in the third memory (add) 263, and the data of reversed wave of the sinusoidal wave are stored in the fourth memory (sub) 264.

Then the maximum amplitude calculator 24 detects the maximum value and the minimum value of the wave data stored in the third memory (add) 263, calculates the difference, which is the maximum amplitude of the wave, and sends the data of the maximum amplitude (which is also referred to as "addition amplitude") aa to the another by Δf are superposed one by one to the one stored in the second memory (wave) 262. When the frequency variable f reaches the upper limit $f_h$, it is determined to be N (No) at Step S14 and the process ends there.

The above method is summarized as follows. In superposing a sinusoidal wave of a frequency, that of 0° phase angle and that of 180° phase angle are compared, and the one causing the smaller maximum amplitude of the superposed wave is selected. And, instead of adding the wave of 180° initial phase angle, the wave of 0° initial phase angle is subtracted. This means that it is sufficient to generate a sole sinusoidal wave to superpose a sinusoidal wave of a frequency, and there is no need to generate a plurality of sinusoidal waves of different initial phase angles.

Evaluation of the above-described broad-band signal generating method is done as follows, where:

the lowest frequency $f_L$: 10 kHz, the highest frequency $f_h$: 455 kHz, frequency step Δf: 1 kHz, and D/A converting speed: 10 MHz.

Thus the duration of a cycle of the superposed wave is 1 msec, and the number n is 10000.

Figure 4:
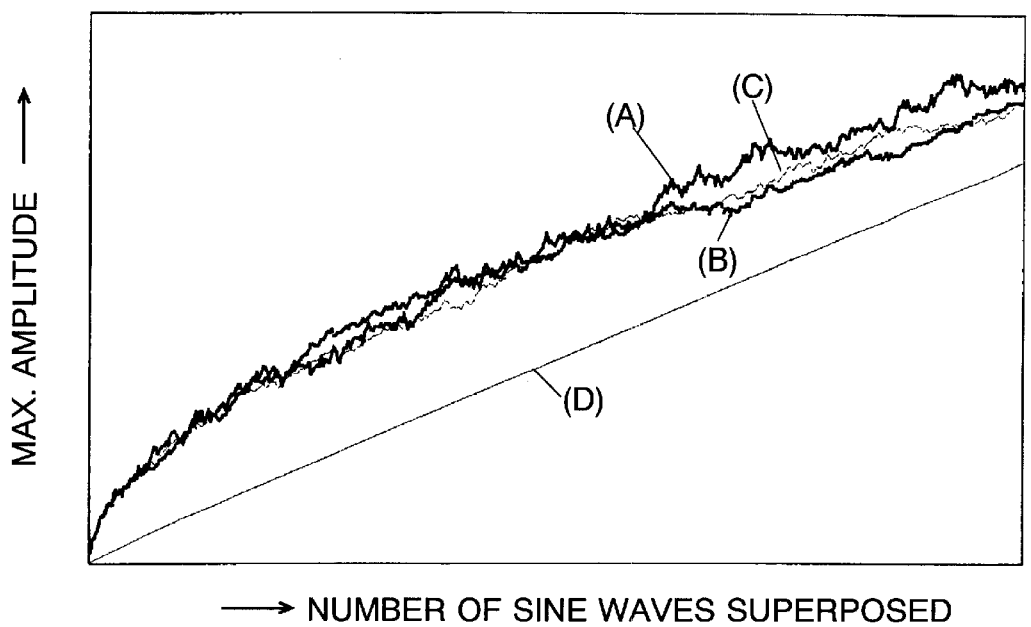
FIG. 4 is a graph showing the growth of the maximum amplitude of the superposed wave with respect to the number of waves superposed.

FIG. 4 is a graph showing the growth of the maximum amplitude of the superposed wave with respect to the number of waves superposed, where the superposition is done from the lower frequency. The graph compares several results including one according to the present embodiment (A), one after search for an optimal initial phase angle with 1.8° phase angle steps (B), one after search with 18° phase angle steps (C) and one without any search for an optimal initial phase angle (D). In the case of the result (D), the scale of the ordinate is shrunk by 1/10, because the result (D) without any search causes an enormous growth of the maximum amplitude of the superposed wave.

It is apparent that, compared to the result (D), the methods of (A), (B) and (C) can suppress the amplitude to about 1/10, and there is no significant difference in the methods of (A), (B) and (C). That is, the method of the present invention has almost the same amplitude suppressing effect or the dynamic range suppressing effect as those by conventional methods which search the optimal initial phase angle with small phase angle steps.

Figure 5:
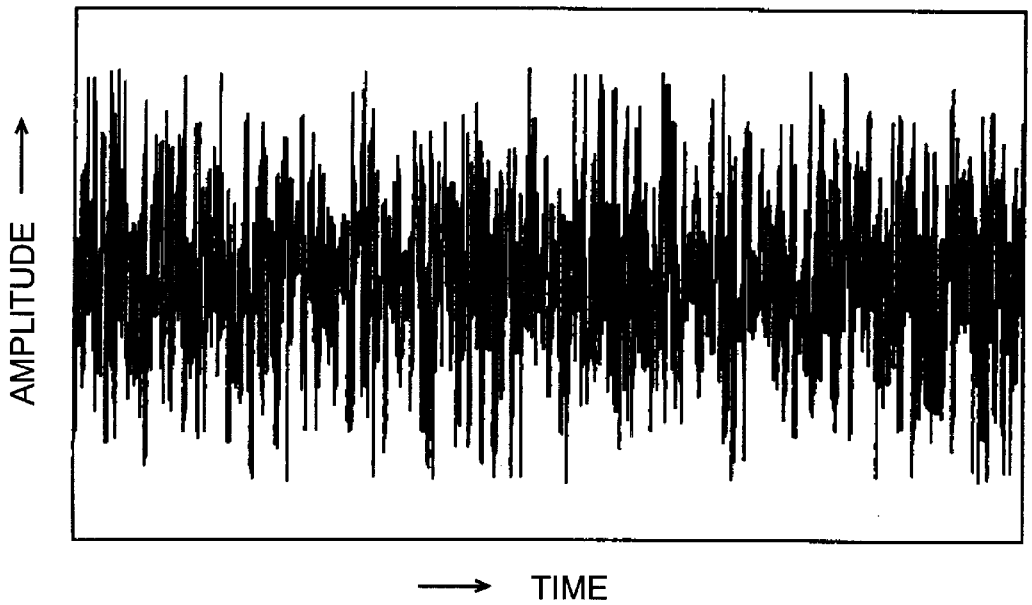
FIG. 5 shows the wave of the broad-band signal constructed by the method of the embodiment.
Figure 6A:
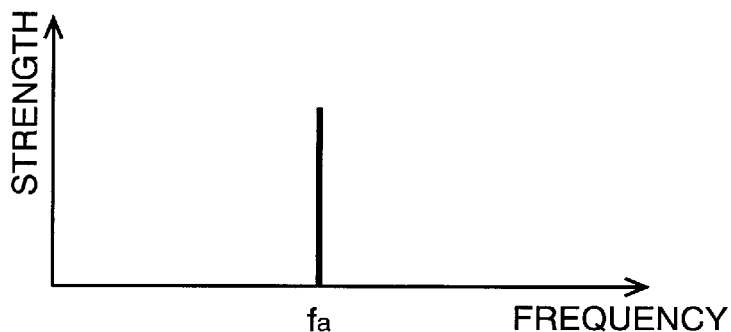
FIGS. 6A–6C show frequency distribution of various voltage signals applied to the end cap electrodes of an ion trap mass spectrometer.
Figure 6B:
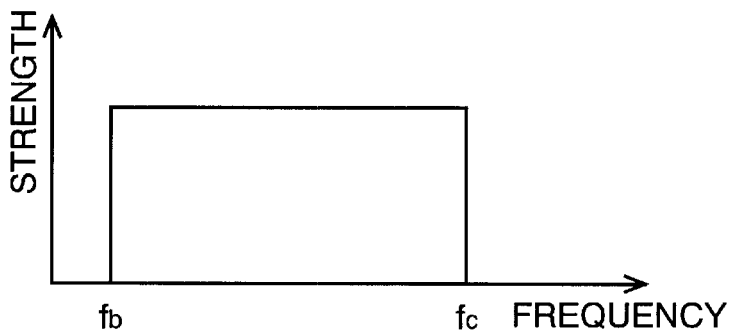
Figure 6C:
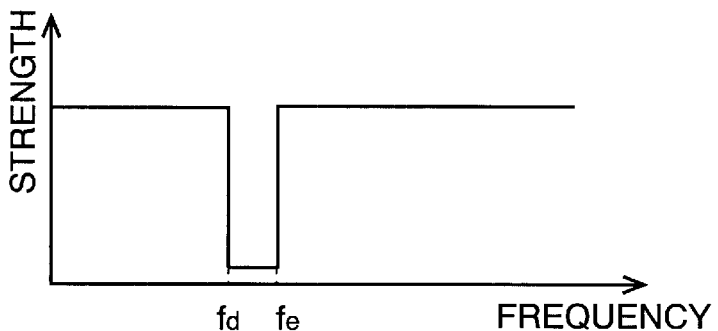

FIG. 5 shows the wave of the broad-band signal constructed by the method of the present embodiment. Such a broad-band signal wave is actually produced and analyzed by a spectrum analyzer, and a satisfying frequency superposition is confirmed without causing any drop or rise of a particular frequency component.

Though, in the above embodiment, the frequencies of the component sinusoidal waves are regularly distributed with the interval of $\Delta f$, it is apparent that the method of the present invention can be applied to the waves of irregularly distributed frequencies. That is, any combination of sinusoidal waves of desired frequencies can be superposed to obtain a superposition of the smallest maximum amplitude according to the present invention.

What is claimed is:

1. A method of producing a broad-band signal including a plurality of component frequencies of regular or irregular intervals, the broad-band signal being used to apply an alternating voltage to end cap electrodes of an ion trap mass spectrometer, the method comprising steps of:
   a) generating a sinusoidal wave having one of the component frequencies;
   b) adding the sinusoidal wave to a current temporary superposed wave to produce an addition wave;
   c) subtracting the sinusoidal wave from the current temporary superposed wave to produce a subtraction wave;
   d) selecting either of the addition wave or the subtraction wave that has a smaller amplitude as a next temporary superposed wave; and
   e) repeating the steps a)–d) for all the component frequencies.

2. An ion trap mass spectrometer comprising:
   a ring electrode;
   a pair of end cap electrodes placed at open ends of the ring electrodes;
   a voltage source for applying an alternating current voltage to the pair of end cap electrodes; and
   a broad-band signal generator for generating a broad-band signal composed of different frequencies by superposing sinusoidal waves each having one of the different frequencies and having either a 0° initial phase angle or a 180° initial phase angle so that an addition of the sinusoidal wave of the 0° initial phase angle or the sinusoidal wave of the 180° initial phase angle brings about a smaller amplitude.

3. An ion trap mass spectrometer according to claim 2, wherein the broad-band signal generator generates the sinusoidal wave of the 180° initial phase angle by reversing the sinusoidal wave of the 0° initial phase angle.

* * * * *